United States Patent
Pham et al.

(10) Patent No.: US 9,138,425 B2
(45) Date of Patent: Sep. 22, 2015

(54) DRUG DELIVERY SYSTEM TO INCREASE BIOAVAILABILITY

(71) Applicant: Patheon Inc., Mississauga (CA)

(72) Inventors: Anh Thu Thi Pham, Mississauga (CA); Akaash Kumari Singh, Toronto (CA); Stefan Proniuk, Weehawken, NJ (US)

(73) Assignee: PATHEON INC., Mississauga (CA)

( * ) Notice: Subject to any disclaimer, the term of this patent is extended or adjusted under 35 U.S.C. 154(b) by 0 days.

(21) Appl. No.: 14/203,674

(22) Filed: Mar. 11, 2014

(65) Prior Publication Data

US 2014/0271872 A1    Sep. 18, 2014

Related U.S. Application Data

(60) Provisional application No. 61/777,733, filed on Mar. 12, 2013.

(51) Int. Cl.
 *A61K 9/20* (2006.01)
 *A61K 31/415* (2006.01)

(52) U.S. Cl.
 CPC .............. *A61K 31/415* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01)

(58) Field of Classification Search
 CPC .. A61K 9/2054; A61K 9/2009; A61K 9/2031
 See application file for complete search history.

(56) References Cited

FOREIGN PATENT DOCUMENTS

| | | |
|---|---|---|
| CA | 2540056 A1 | 4/2005 |
| CA | 2738114 A1 | 4/2010 |
| CA | 2746129 A1 | 6/2010 |
| CA | 2771539 A1 | 2/2011 |
| CA | 2787907 A1 | 7/2011 |
| CA | 2798090 A1 | 12/2011 |
| CA | 2841960 A1 | 1/2013 |
| WO | WO 2008063933 A2 | 5/2008 |

OTHER PUBLICATIONS

Berge, et al., "Pharmaceutical salts", J. Pharm Sci., 66:1, 1977, pp. 1-19.
Benet, et al., "The use of BDDCS in classifying the permeability of marketed drugs", Pharmaceutical Research, 25(3), 2008, pp. 783-488.
Kasim, et al., "Molecular Properties of WHO Essential Drugs and Provisional Biopharmaceutical Classification", Molecular Pharmaceutics, vol. 1, No. 1, 2004, pp. 85-96.
Evonik Industries, "Aerosil and Aeroperl Colloidal Silicon Dioxide for Pharmaceuticals" Technical Information TI 1281, Sep. 2013, 24 pages.
International Search Report and Written Opinion from related PCT Application PCT/CA2014/000207, dated Jun. 17, 2014, 15 pages.

*Primary Examiner* — Carlos Azpuru
(74) *Attorney, Agent, or Firm* — Norton Rose Fulbright US LLP; Scott D. Rothenberger (57) ABSTRACT

A drug delivery system is presented to increase the bioavailability of biopharmaceutic class II, III, or IV active agents.

20 Claims, 4 Drawing Sheets

| Material | Process[1] | Equipment |
|---|---|---|
| Sodium lauryl sulphate<br>BHT or BHA or Ascobic acid<br>API | Preblend [3] | Diffusion blender |
| Colloidal silicon dioxide | Preblend [3] | Diffusion blender |
| Mannitol<br>Microcrystalline cellulose | Preblend [3] | Diffusion blender |
|  | De-lumping | Conical mill |
| Poloxamer 407 [2] | Intragranular Blend | Diffusion blender |
| Microcrystalline cellulose (IG portion) [2]<br>Crospovidone (IG portion) [2] | Intragranular Blend | Diffusion blender |
| Sodium stearyl fumarate[2] | Intragranular Lubrication | Diffusion blender |
|  | Roller Compaction<br>Multiple passes until granulation has a bulk density of > 4.0 g/mL | Roller compactor |
| MCC PH 200 LM (EG portion) [2]<br>Crospovidone (EG portion) [2]<br>Talc [2] | Final Blend | Diffusion blender |
| Sodium stearyl fumarate[2] | Lubrication | Diffusion blender |
|  | Compression | Rotary tablet press |
| Polyvinyl alcohol coating dispersion or<br>Polyvinyl alcohol and polyethylene glycol coating dispersion or<br>Polyvinyl alcohol polyethylene glycol copolymer coating dispersion | Coating (Moisture Barrier) | Perforated pan coater |
| Methacrylic Acid Copolymer Dispersion<br>PEG 8000, Triethyl citrate or Triacetin | Coating (Enteric Coating) | Perforated pan coater |

[1] Process under low humidity (< 20% RH wherever possible)
[2] Material screened through a # 20 mesh
[3] IG = intragranular  EG = extragranular  Opadry AMB (polyvinyl alcohol coating system)/Opadry II 85f (/Kollicoat (Polyvinyl alcohol polyethylene glycol copolymer coating dispersion) These are moisture barrier coating systems  Acryleze 93A (methacrylic acid copolymer dispersion used for enteric coating) and Triethyl citrate (plasticizer for enteric coating.  PEG 8000 and Triacetin are used for the same purpose)

DRUG DELIVERY SYSTEM TO INCREASE BIOAVAILABILITY

CROSS REFERENCE TO RELATED APPLICATION(S)

This application claims priority to U.S. Provisional Application Ser. No. 61/777,733, filed Mar. 12, 2013, the contents of which are incorporated herein in their entirety for all purposes.

FIELD

Aspects described herein relate generally to the development of novel methods and novel delivery systems that can be used to modulate the pharmacokinetics of low solubility and/or hygroscopic pharmaceutically active ingredients. Aspects also relate generally to drug delivery systems that provide, in one aspect, increased utility of class II, III and IV type drugs that typically have low solubility, low permeability or both. Previously, such drugs tended to be difficult to deliver in an efficacious manner, thereby decreasing overall bioavailability of the active ingredient(s).

BACKGROUND

Formulating low solubility therapeutic compounds (e.g., Bioclassification II and IV compounds) can be challenging because of variability in the physical properties of the compound. A formulation which results in acceptable pharmaceutical unit doses using one lot of active compound may produce unacceptable pharmaceutical unit doses with another lot of active compound. In some cases, the compound may be highly cohesive and adhesive which presents a number of processing challenges.

Problems associated with formulations include poor granule quality, poor weight uniformity among doses, and tablets that have a surface damage as a result of challenges during granule compression. Variable product characteristics and density variations resulting from previously known methods may make the product's commercial use impractical.

In recent years, there has been a steady increase in the number of low solubility compounds in drug development. For example, up to approximately 90% of new chemical entities can be categorized as BCS class II or IV compounds. In contrast, more than 50% of marketed drugs are classified as highly soluble. Thus, it is clear that poor compound solubility is a major hurdle for formulators of new chemical entities. Oral bioavailability of insoluble compounds may be improved by optimizing the API's chemical (e.g., salt formation) and physical (e.g., particle size reduction through milling) properties. However, the increased number of compounds in development and the shortened timelines for formulation development require a more efficient approach using computational tools in place of or in addition to empirical approaches typically employed to study API effect on bioavailability, such as in vivo studies in animal models. Computational tools may also provide a mechanistic link between API properties and bioperformance.

Absorption estimates such as the maximum absorbable dose calculation or the absorption potential proposed by Dressman et al. can be used to link the solubility of compound to the expected extent of oral absorption. Such estimates would appear suitable for early decisions on API phase selection as far as overall exposure is concerned. However, formulation development is frequently driven by specific pharmacokinetic and pharmacodynamic needs (e.g., rapid solubilization of drugs for fast onset of action), in which case more detailed models are needed to account for the rate of dissolution as well as the linkage between absorption and pharmacokinetic profile. Similarly, when trying to understand effect of API bulk properties on formulation bioperformance, models that can account for the effect of API on dissolution rate are needed to guide formulation efforts.

Thus, there is a need for a method to deliver drugs that minimize or overcome the above-referenced problems. There is also a need for a simple manufacturing process utilizing existing conventional equipment to lower manufacturing costs.

BRIEF SUMMARY

Aspects described herein relate to methods of treating diseases, dosage forms, and methods of modulating the pharmacokinetics of active ingredients.

In some aspects, methods of making the solid pharmaceutical dosage forms are provided.

Aspects described herein provide new delivery systems that are useful, for example, for increasing the bioavailability and/or dissolution of biopharmaceutic class II, III or IV active agents. In another aspect, the delivery system reduces the intra and interpatient pharmacokinetic variability and/or prevents gel formation when the composition that contains the biopharmaceutic agent is exposed to an aqueous environment, such as water or body fluids (e.g., blood, saliva, gastrointestinal fluid, etc.).

In one aspect, the delivery system compositions include, for example, a nonionic triblock copolymer, or a nonioinic triblock copolymer and a polyethylene glycol (in combination with the biopharmaceutic class II, III or IV active agent(s)). In another aspect, the triblock copolymer includes a central hydrophobic chain of polyoxypropylene having a first end and a second end, wherein two hydrophilic chains of polyoxyethylene are attached to the first and second ends of the polyoxypropylene.

In another aspect, the delivery system further includes the nonionic triblock copolymer as described above and sodium lauryl sulfate.

In addition to the sodium lauryl sulfate, the delivery system can include additional components for preventing or minimizing gel formation (e.g., silicon dioxide, citric acid, ascorbic acid, magnesium oxide, sodium carbonate and sodium acetate). In one aspect, the selection of these additional components will consider variables such as the pH at which the API agent is completely insoluble in order to prevent hydration before the dosage form completely disintegrates.

In still another aspect the delivery systems described above can also include a crosslinked polyvinylpyrrolidone.

In still another aspect, micronization of the biopharmaceutic class II, III or IV active agent(s) in combination with the delivery systems described herein can improve bioavailability, dissolution rate, intra and inter-patient pharmacokinetic variability and/or gelling. For example, micronization can further enhance the dissolution rate and/or bioavailability by increasing the surface area of the agent.

Exemplary compositions disclosed herein can be prepared in tablet form or, alternatively, can be filled into two piece capsules.

While multiple aspects are disclosed, still other aspects will become apparent to those skilled in the art from the following detailed description. As will be apparent, these aspects can be modified without departing from the spirit and scope of the description herein. Accordingly, the detailed descriptions are to be regarded as illustrative in nature and not restrictive.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In addition, the materials, methods, and examples are illustrative only and not intended to be limiting.

Other features and advantages will be apparent from the following detailed description, and from the claims.

BRIEF DESCRIPTION OF THE DRAWINGS

FIG. 4 provides another workflow diagram of a process to prepare a capsule described herein.

DETAILED DESCRIPTION

Aspects described herein relate to methods of treating diseases, dosage forms, and methods of modulating the pharmacokinetics of active ingredients.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention.

As used herein, the recitation of a numerical range for a variable is intended to include any of the values within that range. Thus, the variable can be equal to and include any integer value within the numerical range, including the endpoints of the range. Similarly, the variable can be equal to any real value within the numerical range, including the endpoints of the range. As an example, a variable which is described as having values between 0 and 2 can take the values 0, 1 or 2 can take the values 0.0, 0.1, 0.01, 0.001, or any other real values ≥0 and ≤2.

Any method of making a solid pharmaceutical dosage form, such as those disclosed in *Remington: The Science and Practice of Pharmacy*, Twenty-First Ed. (Philadelphia, Pa.: Lippincott Williams & Wilkins, 2005), the contents of which are incorporated by reference herein in their entirety, may be used to make the solid pharmaceutical dosage forms described herein.

Aspects described herein provide delivery systems for, in particular, active ingredients that have properties associated with Biopharmaceutics Class II, Class III or Class IV active ingredients as taught by Leslie Z. Benet; Gordon L. Amidon, Dirk M. Barends; Hans Lennernas; James E. Polli; Vinod P. Shah; Salomon A. Stavchansky; Lawrenced X. Yu, "The use of BDDCS in classifying the permeability of marketed drugs", Pharmaceutical Research 2008, 25(3); 483-488 and Nehal A. Kasim, Marc Whitehouse, Chandrasekharan Ramachandran, Marival Bermejo, Hans Lennernals, Ajaz S. Hussain, Hans E. Junginger, Salomon A. Stavchansky, Kamal K. Midha, Vinod P. Shah and Gordon L. Amidon, "Molecular Properties of WHO Essential Drugs and Provisional Biopharmaceutical Classification", Molecular Pharmaceutics, vol 1, No 1, 85-96, 2004, the contents of which are incorporated herein in their entirety for all purposes.

The phrase "biopharmaceutic class II, III or IV active agent" refers to the Biopharmaceutics Classification System (BCS) that is used as a guide for predicting the intestinal drug absorption provided by the U.S. Food and Drug Administration. The basis for the BCS was established by Dr. Gordon Amidon as noted above. This system uses solubility and intestinal permeability to predict intestinal drug absorption. The solubility classification is based on a United States Pharmacopoeia (USP) aperture. The intestinal permeability classification is based on a comparison to the intravenous injection. All those factors are highly important, since 85% of the most sold drugs in the USA and Europe are orally administered.

According to the Biopharmaceutics Classification System, drug substances are classified as follows:

Class I—High Permeability, High Solubility

Examples of Class I biopharmaceutics are known in the art and include, but are not limited to, metoprolol, metoprolol tartrate, propanolol HCl and acetaminophen.

Those compounds are well absorbed and their absorption rate is usually higher than excretion.

Class II—High Permeability, Low Solubility

Examples of Class II biopharmaceutics are known in the art and include, but are not limited to, glibenclamide, naproxen, ketoprofen, carbamazepine, tacrolimius, ketoconazole, nifedipine and/or felodipine.

The bioavailability of those products is limited by their solvation rate. A correlation between the in vivo bioavailability and the in vitro solvation can be found, for example, in Kasim et al, *Molecular Properties of WHO Essential Drugs and Provisional Biopharmaceutical Classification*, Molecular Pharmaceutics, Vol. 1, No. 1, 85-96 (Dec. 17, 2003), hereby incorporated by reference in its entirety.

Class III—Low Permeability, High Solubility

Examples of Class III biopharmaceutics are known in the art and include, but are not limited to, ranitidine, acyclovir, enalaprilate and/or alendronate.

The absorption is limited by the permeation rate but the drug is solvated very fast. If the formulation does not change the permeability or gastro-intestinal duration time, then class I criteria can be applied.

Class IV—Low Permeability, Low Solubility

Examples of Class IV biopharmaceutics are known in the art and include, but are not limited to, hydrochlorothiazide, chlorothiazide, furosemide, methotrexate and/or tobramycin.

Class IV compounds have a poor bioavailability. Usually they are not well absorbed over the intestinal mucosa and a high variability is expected.

The following BCS class drugs (log P-based) are included herein as examples of active ingredients that can be used with the delivery systems described herein. The number (x) which follows the active ingredient identifier is the log P-based classification. Such active ingredients include, but are not limited to, abacavir sulfate (3), acetazolamide (4), acetylsalicylic acid (3), acyclovir (3), albendazole (2), allopurinol (4), amiloride hydrochloride (3), amoxicillin artemether (3), atenolol (3), atropine sulfate (3), captopril (3), carbamazepine (2), chloramphenicol (3), cimetidine (3), ciprofloxacin hydrochloride (3), clofazimine (2), codeine phosphate (3), colchicine (3), dapsone (4), dexamethasone (3), diazepam (2), didanosine (3), diethylcarbamazine citrate (3), diloxanide furoate (2), doxycycline (4), efavirenz (2), ergometrine maleate (3), ethambutol hydrochloride (3), ethosuximide (3), fluconazole (3), folic acid (3), furosemide (4), glibenclamide (2), griseofulvin (4), haloperidol (2), hydralazine hydrochloride (3), hydrochlorothiazide (3), ibuprofen (2), isoniazid (3), lamivudine (3), lopinavir (with ritonavir) (2), mebendazole (chewable) (2), metformin hydrochloride (3), methotrexate (3), methyldopa (3), metoclopramide hydrochloride (3), nalidixic acid (4), nevirapine (2), niclosamide (chewable) (2), nifedipine (2), paracetamol (4), penicillamine (3), penicillin V potassium (3), phenobarbital (3), phenyloin (chewable) (2), praziquantel (2), primaquine phosphate (3), propylthiouracil (3), pyrantel embonate (2), pyrazinamide (3), pyridoxine hydrochloride (3), pyrimethamine (4), retinol palmitate (2), ritonavir (2), salbutamol sulfate (3), spironolactone (2), stavudine (3), sulfadiazine (4), sulfamethoxazole (4), sulfasalazine (2), theophylline (4), trimethoprim (4), valproic acid (3).

The pharmaceutical composition can be provided as a salt of the active agent where applicable. Salts are more soluble in aqueous or other protonic solvents than the corresponding free acid or base forms. Pharmaceutically acceptable salts are well known in the art. Active ingredients may form pharmaceutically acceptable acid addition salts with suitable acids. For example, Berge et al., *J Pharm Sci*, 66:1 (1977), describe pharmaceutically acceptable salts in detail. Representative acid addition salts include, but are not limited to, acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate or sulfate, nicotinate, 2-naphthalenesulfonate, oxalate, pamoate, pectinate, persulfate, 3-phenylpropionate, picrate, pivalate, propionate, succinate, tartrate, thiocyanate, phosphate or hydrogen phosphate, glutamate, bicarbonate, p-toluenesulfonate, and undecanoate. Examples of acids that can be employed to form pharmaceutically acceptable acid addition salts include, without limitation, such inorganic acids as hydrochloric acid, hydrobromic acid, sulfuric acid, and phosphoric acid, and such organic acids as oxalic acid, maleic acid, succinic acid, and citric acid.

In one aspect, the compositions and formulations provided herein are formulated for oral administration. In another aspect, the composition is an orally administered, solid formulation. While previous formulations produced tablets that were inconsistent in bioavailability, and materials that were difficult to handle even for inclusion into gelatin capsules of suitable size, the compositions described herein provide unit dosages that can be produced consistently and in suitable sizes for convenient oral administration.

Suitable pharmaceutically acceptable excipients of the pharmaceutical composition include, but are not limited to, binders, diluents, disintegrants, lubricants, glidants, fillers, carriers, and the like.

Binders are used to impart cohesive qualities to a tablet formulation, and thus ensure that a tablet remains intact after compaction. Suitable binder materials include, but are not limited to, cellulose, microcrystalline cellulose (such as AVICEL®, e.g. AVICEL® 102), gelatin, sucrose, glucose, dextrose and maltodextrin, polyethylene glycol, waxes, natural and synthetic gums, cross-linked polyvinylpolypyrrolidone (Crospovidone), copolymers of vinylpyrrolidone and vinyl acetate (Copovidone), cellulosic polymers (including hydroxypropyl cellulose, methyl cellulose, hydroxyethyl cellulose, and the like), lactose (Lactose Fast Flo).

Polyvinylpyrrolidone (Povidone) and cross-linked polyvinylpolypyrrolidone (crosspovidone) are known as crospospovidone, available from BP, PhEur and USP-NF. These may also be known, for example, as povidone, Kollidon, Plasdone, and crospovidone.

In another aspect, the phrase "crosslinked polyvinylpyrrolidone" (PVP) is intended to include a water-soluble polymer made from the monomer N-vinylpyrrolidone. Other names associated with such materials include, for example, Crospovidonum; Crospopharm; crosslinked povidone; E1202; Kollidon CL; Kollidon CL-M; Polyplasdone XL; Polyplasdone XL-10; polyvinylpolypyrrolidone; PVPP; 1-vinyl-2-pyrrolidinone homopolymer.

Polyvinylpolypyrrolidone (PVPP, crospovidone) is a highly cross-linked modification of PVP. Suitable PVPP's include Kollidon CL from BASF or Polyplasdone XL-10 from ISP. In one aspect, high concentrations of PVPP are important for exemplary formulations of the delivery system described herein. In one aspect, at least about 1% to about 40% by weight more particularly at least about 5% to about 25% by weight of PVPP is included in the tablet. In another aspect, from about 5 to about 10 weight percent PVPP is provided and in yet another aspect, from about 10 to about 12 weight percent is provided. In yet another aspect, from about 10 to about 25 weight percent PVPP is provided. Previously known tablets generally include about 2 to about 5 weight percent of PVPP of the total weight basis of the tablet. Without being limited by theory, it is believed that the increased percentages of PVPP (relative to standard tablets) helps prevent hydration of the API and gelling within the tablet composition. Hydration of the API and gelling of the tablet formulation decreases the dissolution rate and bioavailability of the active agent. In one aspect, crospovidone was the most effective in disintegrating the tablets rapidly before the active agent hydrates and starts to gel. When other disintegrants (e.g., croscarmellose or sodium starch glycolate) were used, the tablet still gelled.

Unlike other superdisintegrants, which rely principally on swelling for disintegration, crospovidone uses a combination of mechanisms to provide rapid disintegration. Although crospovidone polymers swell by 95% to 120% upon contact with water, swelling is not the only mechanism for tablet disintegration.

Crospovidone polymers, with their porous particle morphology, will rapidly absorb water (wicking) via capillary action. During tablet compaction, the highly compressible crospovidone particles become highly deformed. As the deformed crospovidone particles come in contact with water that is wicked into the tablet, the crospovidone particles recover their normal structure and swell, resulting in rapid volume expansion and hydrostatic pressures that cause tablet disintegration.

Additionally, crospovidone is a good binder and it counters the effect of high silicon dioxide content on tablet compressibility.

The phrase "N-vinylpyrrolidone/vinyl acetate copolymer" refers to a water soluble polymer made from the copolymerization of N-vinylpyyrolidone with vinyl acetate. "Copovidone" is available from BASF.

In one aspect, the composition comprises about 5% to about 60% of binder by weight. The term "binder" in certain aspects refers to a substance that improves compression and promotes association between individual particles after compression. Binders can be used, for example, for dry granulation and direct compression, or dissolved in water or a solvent for use in wet granulation. Common binders include saccharides, gelatins, pregelatinized starches, microcrystalline cellulose, hydroxypropylcellulose and cellulose ethers, as well as polyvinylpyrrolidone (PVP).

In another aspect, the composition comprises about 7% to about 50% of binder by weight. In another aspect, the composition comprises about 10% to about 60% of binder by weight. In another aspect, the composition comprises about 10% to about 20% of binder by weight. In yet another aspect, the composition comprises about 20% to about 50% of binder, such as microcrystalline cellulose, by weight.

In one aspect, the composition of the invention comprises a diluent or bulking agent. Exemplary diluents or bulking agents may be one or more compounds which are capable of providing compactability and good flow. A variety of materials may be used as fillers or diluents. Suitable diluents or fillers include, but are not limited to, sucrose, dextrose, sorbitol, starch, cellulose (e.g. microcrystalline cellulose; Avicel®), dihydrated or anhydrous dibasic calcium phosphate, calcium carbonate, calcium sulfate, and others as known in the art.

Some excipients function as both a binder and a diluent, such as microcrystalline cellulose and starch.

In one aspect, pharmaceutical lubricants and glidants are designed to promote smooth, effortless tablet ejection during manufacturing. The flow of the tablet powder blend is improved by the lubricant by, for example, reducing interparticle friction. Antiadherents are specific lubricants that prevent the tablet powder from sticking to the metal components of the punch press during manufacturing. Lubricants can be hydrophobic, such as magnesium stearate, or hydrophilic. Other common glidants and lubricants include mineral oils, talcs, and sodium stearyl fumarate. In another aspect, glidants may be used to increase powder flow. In yet another aspect, lubricants may be used to increase powder flow and also prevent "sticking" of particles during compression.

Lubricants can be employed herein in the manufacture of certain dosage forms, and will usually be employed when producing granules and tablets. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax™ for polyethylene glycol and Polyox™ for polyethylene oxide from Dow Chemical Company, Midland, Mich.), sodium lauryl sulfate, magnesium lauryl sulfate, sodium oleate, sodium stearyl fumarate, DL-leucine, colloidal silicon, and others as known in the art. In some embodiments, the lubricant is magnesium stearate or sodium stearyl fumarate.

Lubricants may comprise from about 0.5 wt % to about 5 wt % of the granule weight. In some aspects, the composition comprises about 1% to 5% by weight of lubricant. In some aspects, the composition comprises about 0.5% to about 4% by weight of lubricant. In some aspects, the composition comprises about 1% to about 5% by weight of lubricant. In yet another aspect, the composition comprises about 0.5% to about 3% by weight of lubricant.

In some aspects, the composition comprises about 5% to about 25% of disintegrant by weight. In one aspect, disintegrants are added to pharmaceutical formulations to aid in their breakage and dispersion into a wet environment, e.g., the human digestive tract. Pharmaceutical disintegrants act by increasing swelling, increasing porosity, or causing deformation of the tablet. Common disintegrants include starches, crosspovidone, and modified cellulose. Superdisintegrants are disintegrants that act in tandem to accelerate the tablet disintegration process. For example, the behavior of crosspovidine in complement with croscarmellose sodium wicks away liquid, resulting in swelling of the tablet, leading to disintegration.

In some aspects, the composition comprises about 10% to about 20% of disintegrant by weight. In some aspects, the composition comprises about 10% to about 15% of disintegrant by weight. In some aspects, the composition comprises about 12% to about 15% of disintegrant by weight. In yet another aspect, the composition comprises about 7% to about 15% of disintegrant by weight.

Suitable glidants include magnesium trisilicate, powdered cellulose, starch, talc, tribasic calcium phosphate, stearate salts and colloidal silicon dioxide. In some aspects, the glidant is talc, specifically purified talc, and/or colloidal silicon dioxide. In the aspects described herein, it was unexpectedly found that the use of a relatively large amount of colloidal silicon dioxide was successful in improving physical properties of the tablet. In one aspect, replacing Avicel, lactose, L-HPC (low substituted hydroxypropyl cellulose) with silicon dioxide and optimizing the quantities, provides a satisfactory formulation that prevents gelling resulting in increased drug release and improved bioavailability. The quantities of silicon dioxide can be optimized, for example, by adding different concentrations of silicon dioxide added to a formulation, measuring the dissolution rate, and further testing of the formulation in animal pharmacokinetic studies. In one aspect, if the percentage of silicon dioxide is not sufficient, the tablet will form a gel and the formulation will not achieve rapid or complete disintegration resulting in a slower release of the drug. In another aspect, higher concentration of silicon dioxide may require adjustments to the manufacturing process to obtain desired density and flow for processing (e.g., multiple roller compaction passes).

Silicon dioxide can be included in the delivery systems disclosed herein. Suitable silicon dioxide includes, but is not limited to, colloidial silicon dioxide. Suitable amounts of silicon dioxide added to the delivery systems described herein range from about 2 to about 40 weight percent, from about 5 to about 20 and more particularly from about 7 to about 10 percent, e.g., 10, 15, 20, 25, 30, 35, 40 percent based on the total weight basis of a tablet.

Previously, tablets contained from about 0.2 to about 1% silicon dioxide of the total weight of a tablet. In contrast, the present invention utilizes significantly more glidant, (e.g., silicon dioxide) than current practices. Without being limited by theory, it is believed that use of from about 4% to about 40% by weight of a glidant (e.g., silicon dioxide) helps improve the bioavailability of biopharmaceutic class II, III or IV active agents. It is believed that a higher amount of a glidant increases desiccation of the microenvironment of a hygroscopic API, preventing formation of a gel mass which could decrease the rate of API release and bioavailability. It has been discovered that relatively high amounts of silicon dioxide, e.g., colloidal silicon dioxide, (approximately 10 weight percent of total weight of capsule, e.g., 10, 11, 12, 13, 14, 15, 16, 17, 18, 19, 20, 15-20, 15-25, 30, 40 weight percent) can substantially reduce or prevent a Pharmaceutically Acceptable Salt from agglomerating, gelling or sticking. It is believed that colloidal silicon dioxide acts as an anti-gellant in the formulation and prevents sticking during manufacturing. The conventional use of silicon dioxide in pharmaceutical formulations is as a glidant to assist in the flow powder during manufacturing, not as an anti-gelling material.

In another aspect, ascorbic acid, citric acid or other suitable acids can be used in addition to silicon dioxide to provide a microenvironment to keep an API that is insoluble in acidic media dessicated. Generally, an acid, such as ascorbic acid is used with a biopharmaceutic class II, III or IV active agent that has a carboxylic acid or other acidic functionality. Suitable amounts of acids range from about 0.2% to about 2%, more particularly from about 0.5% to about 1.5% and most particularly from about 0.7% to about 1% based on the total weight of the tablet.

In another aspect, a base can be used in addition to silicon dioxide in formulations for biopharmaceutic class II, III or IV active agents that are basic. It is believed that the combination of a base and silicon dioxide provides a microenvironment that minimizes hydration such that active agent remains dry until released into the patient's body.

In other aspects, the composition comprises about 1% to about 10% of a polyoxyethylene-polyoxypropylene copolymer (a poloxamer) by weight. In some aspects, the composition comprises about 2% to about 8% of poloxamer by weight. In some aspects, the composition comprises about 1% to about 5% of poloxamer by weight. In some aspects, the composition comprises about 3% to about 7% of poloxamer by weight. In some aspects, the composition comprises about 5% to about 10% of poloxamer by weight. In some aspects, the composition comprises about 7% to about 10% of poloxamer by weight.

Nonionic triblock copolymers utilized with the delivery systems described herein include "Poloxamers" which are nonionic triblock copolymers composed of a central hydrophobic chain of polyoxypropylene (poly(propylene oxide)) flanked by two hydrophilic chains of polyoxyethylene (poly(ethylene oxide)). The word "poloxamer" was coined by the inventor, Irving Schmolka. Poloxamers are also known by the trade name "PLURONIC".

Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

Poloxamers are considered to function as dispersing agents; emulsifying agents; solubilizing agents; tablet lubricants; or wetting agent. Suitable poloxamers (α-hydro-ω-hydroxypoly(oxyethylene)poly(oxypropylene)poly(oxyethylene) block copolymers) include, for example, Lutrol; Monolan; Pluronic; poloxalkol; poloxamera; polyethylene-propylene glycol copolymer; polyoxyethylene-polyoxypropylene copolymer; Supronic; and Synperonic.

The poloxamer polyols are a series of closely related block copolymers of ethylene oxide and propylene oxide conforming to the general formula $HO(C_2H_4O)_a(C_3H_6O)_b(C_2H_4O)_a \cdot H$. A general structural formula provides:

for poloxamers.

The delivery systems disclosed herein can further include polyethylene glycol (PEG) or SLS. Suitable PEG's include those with a molecular weight sufficient to exist in solid form.

In further aspects, the composition comprises one or more pharmaceutically acceptable excipients selected from the group consisting from colloidal silicon dioxide; crospovidone; copovidone, sodium lauryl sulfate, microcrystalline cellulose, lactose (Fast Flo), and sodium stearyl fumarate. In some aspects, the pharmaceutical composition comprises one or more pharmaceutically acceptable excipients other than compression grade lactose. Other excipients optionally include flavorants and sweeteners; colorants or pigments, e.g., to identify the product or to characterize the quantity (dosage) of active compound; and other ingredients, such as preservatives, stabilizers, salts for regulating osmotic pressure, and buffers.

The term 'blending' means the process of mixing the pharmaceutically active ingredient with at least one excipient. Blending may be conducted through, for example, high shear blending, low shear blending, tumble blending or a combination thereof. High shear blending involves high speed mixing with an impeller blade. The dilation and expansion in material volume ultimately promotes diffusion. The impeller blades also aid mixing by breaking up clumps of cohesive material. Examples of a low shear apparatus V-blender, tote blender, double cone blender or any other apparatus capable of functioning under preferred low shear conditions. Tumble blending involves mixing by tumbling action, it is a gentle mixing action which generates very limited aeration.

The term 'blend' or "formulation blend", as used herein, refers to a generally homogeneous mixture of the pharmaceutically active ingredient and at least one pharmaceutically acceptable excipient. In some aspects, the blend comprises the composition of the present invention.

To prepare the blend, the various components may be weighed, delumped and combined. The components of the blend, including the pharmaceutically active ingredient and the excipient(s), may be combined by blending, mixing, stirring, shaking, tumbling, rolling or by any other methods of combining the formulation components to achieve a homogeneous blend. In one aspects for preparing the blend, the components are weighed and placed into a blending container. Blending is performed for a period of time to produce a homogenous blend using suitable mixing equipment. Optionally, the blend is passed through a mesh screen to delump the blend. The screened blend may be returned to the blending container and blended for an additional period of time. A quadro comil and screen can also be used to delump the mixture. A lubricant may then be optionally added and the blend mixed for an additional period of time. The blend may be directly compressed to form a tablet to form a unit dosage, filled into a capsule to form a unit dosage, formulated into a granule for further processing, or stored. In some aspects, the formulation blend is directly encapsulated in a capsule.

In some aspects, the blend can be formulated with flow and density characteristics suitable for reproducibly filling an empty capsule with a pharmaceutical composition provided herein such that the weight of the filled capsules are essentially uniform. In some aspects, the blend can be formulated with flow and density characteristics suitable for filling an empty capsule with a pharmaceutical composition provided herein such that the weight of the filled capsule is within a maximum and minimum weight. In still other aspects the blend is roller compacted to improve the density and flow suitable for encapsulation or compression. In other aspects, a batch of capsules filled with a composition provided herein are characterized by a mean weight of 595 mg±3.5% and individual weight of 595±5%.

As used herein, a "unit dosage" comprises a dose to be administered in a single dosing event. Aspects described herein provide a pharmaceutical unit dosage formulation, comprising a pharmaceutical composition described herein. In some aspects, the unit dosage comprises the compound as described herein or a pharmaceutically acceptable salt or solvate thereof, in an amount between 25 and 150 mg. In some aspects, the active ingredient or a pharmaceutically acceptable salt or solvate thereof, is in an amount between 50 and 300 mg. In some aspects, the active ingredient or a pharmaceutically acceptable salt or solvate thereof, is in an amount between 75 and 150 mg. In some aspects, the active ingredient or a pharmaceutically acceptable salt or solvate thereof, is in an amount between 125 and 300 mg. In some aspects, the active ingredient or a pharmaceutically acceptable salt or solvate thereof, is in an amount between 130-200 mg. In some aspects, the active ingredient or a pharmaceutically acceptable salt or solvate thereof, is in an amount between 140-160 mg. In further aspects, the active ingredient or a pharmaceutically acceptable salt or solvate thereof, is about 150 mg.

Aspects described herein provide a pharmaceutical unit dosage formulation consisting essentially of about 5% to about 50% w/w active ingredient loading.

In another aspects, the unit dosage consists of this composition and is contained in a gelatin capsule of size 0, as defined herein.

In further aspects, the pharmaceutical unit dosage formulation described herein is a solid, oral formulation. In some aspects, the unit dosage is in the form of a tablet, capsule, or powder. In some aspects, the pharmaceutical composition is encapsulated in a gelatin capsule. Exemplary gelatin capsules include push-fit capsules made of gelatin, as well as soft, sealed capsules made of gelatin and a coating such as glycerol or sorbitol. In certain aspects, the unit dosage comprises a pharmaceutical composition described herein encapsulated in a hard gelatin capsule. In certain aspects, the capsule size is 0 as defined herein. In other embodiments, the capsule size is 1, 2, 3, 4 or 5 as defined herein. In other embodiments, the capsule size is 0, 1, 2, or 3 as defined herein. In alternative embodiments, the capsule size is 00 as defined herein. In some embodiments the capsule size is 00, 0, 1, 2, 3, 4 or 5 as defined herein. In another aspect, the capsule size selected should accommodate a desirable amount of active ingredient and be comfortable for the average human to comfortably swallow. In addition, the capsule size should permit filling of the empty capsule with a pharmaceutical composition provided herein such that the weight of the filled capsule may be essentially uniformly reproduced. In some aspects, the exact dimensions and volume of the capsule are within 10% of the definitions shown below.

| Capsule Size | Outer Diameter (mm) | Height or Locked Length (mm) | Actual Volume (mL) |
|---|---|---|---|
| 000 | 9.91 | 26.14 | 1.37 |
| 00 | 8.53 | 23.30 | 0.95 |
| 0 | 7.65 | 21.7 | 0.68 |
| 1 | 6.91 | 19.4 | 0.50 |
| 2 | 6.35 | 18.0 | 0.37 |
| 3 | 5.82 | 15.9 | 0.30 |
| 4 | 5.31 | 14.3 | 0.21 |
| 5 | 4.91 | 11.1 | 0.13 |

Encapsulation of the pharmaceutical composition described herein provides an alternative to tablets formed from direct compression. The pharmaceutical composition to be encapsulated may be granules made by dry granulation, or formulation blends. In some aspects, the pharmaceutical composition encapsulated is a formulation blend. The term 'direct encapsulation' refers to the process of encapsulation of formulation blends directly into capsules, without the need for granulation. Encapsulation may be carried out, for example, with the fully automated Zanasi LZ 64 encapsulation machine, using the size '0' capsule shells as defined herein.

Aspects described herein provide compositions and formulations to be administered to mammalian subjects. In certain aspects, the subject is a human subject.

Aspects described herein provide compositions and formulations to be administered to mammalian subjects. In certain aspects, the subject is a human subject.

"Treating" as used herein refers to preventing a condition from occurring in a subject that can be predisposed to the disorder, but has not yet been diagnosed as having it; inhibiting the condition, i.e., arresting its development; relieving the condition, i.e., causing its regression; or ameliorating the condition.

Pharmaceutical compositions and pharmaceutical unit dosages described herein can be prepared, placed in an appropriate container, and labeled for treatment of an indicated condition. Accordingly, aspects described herein provide an article of manufacture, such as a container comprising a dosage form of a compound of the invention and a label containing instructions for use of the compound. Further aspects described herein provide kits. For example, a kit can comprise a dosage form of a pharmaceutical composition and a package insert containing instructions for use of the composition in treatment of a medical condition. In either case, conditions indicated on the label can include treatment of pain.

The term "pharmaceutically acceptable" means that which is generally safe, non-toxic and neither biologically nor otherwise undesirable and includes that which is acceptable for human pharmaceutical use as well as veterinary use.

The term "about" means a value that is ±10% or less of the indicated value. For example, "about 150 mg" includes a range that is ±10%, or ±15 mg, of 150 mg. Thus, "about 150 mg" means a range of 135 mg to 165 mg.

The materials for the aspects described herein can be purchased or prepared by a variety of procedures well known to those of ordinary skill in the art. Crospovidone was obtained from BASF or ISP. Collodial silicon dioxide was obtained from Evonik Industries or Cabot. PEGs and Copovidone were supplied by BASF. Lactose was purchased from Foremost Farms.

Suitable excipients include, by way of non-limiting example: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch, using, e.g., maize starch, wheat starch, rice starch, potato starch, gelatin, tragacanth, methyl cellulose, sodium carboxymethylcellulose, polyethylene oxide, and/or polyvinyl pyrrolidone. If desired, disintegrating agents may be added, such as the above-mentioned starches and also carboxymethyl-starch, cross-linked polyvinyl pyrrolidone, croscarmellose, or alginic acid or a salt thereof, such as sodium alginate. Auxiliaries may be included, such as for example, flow-regulating agents and lubricants, e.g., silica, talc, stearic acid or salts thereof, such as magnesium stearate or calcium stearate, and/or polyethylene glycol. In order to produce coatings, solutions of suitable cellulose preparations, such as cellulose ethers, cellulose esters, poly methacrylate and poly acrylate derivatives, may be used. Dye stuffs or pigments may be added to the solid unit dosage forms for identification or in order to characterize dose combinations of active pharmaceutical ingredient(s). Flavoring and masking agents can be incorporated to improve taste, or mask unpleasant tastes associated with the active pharmaceutical ingredients ("API").

The following paragraphs, numbered 1 through 36 provide for various aspects of the present embodiments. In one embodiment, in a first paragraph (1), a drug delivery system is presented. The drug delivery system includes:
sodium lauryl sulfate or a polyethylene glycol;
cellulose;
lactose;
polyvinylpyrrolidone;
a copolymer of polyvinylpyrrolidone and vinyl acetate;
a silicon dioxide;
and sodium stearyl fumarate or magnesium stearate.

2. The drug delivery system of paragraph 1, wherein the cellulose is microcrystalline cellulose.

3. The drug delivery system of either of paragraphs 1 or 2, wherein the lactose comprises a particle size distribution of approximately 75 microns to about 100 microns.

4. The drug delivery system of any of paragraphs 1 through 3, wherein the silicon dioxide is a colloidal silicon dioxide.

5. The drug delivery system of any of paragraphs 1 through 4, wherein the sodium lauryl sulfate or polyethylene glycol is present in an amount of from about 0.5% to about 6% weight percent, wherein the total components equal 100 weight percent.

6. The drug delivery system of any of paragraphs 1 through 4, wherein the cellulose is present in an amount of from about 20 weight percent to about 70 weight percent, wherein the total components equal 100 weight percent.

7. The drug delivery system of any of paragraphs 1 through 4, wherein the lactose is present in an amount of from about 10 weight percent to about 40 weight percent, wherein the total components equal 100 weight percent.

8. The drug delivery system of any of paragraphs 1 through 4, wherein the polyvinyl pyrrolidone is present in an amount of from about 5% to about 25% weight percent, wherein the total components equal 100 weight percent.

9. The drug delivery system of any of paragraphs 1 through 4, wherein the copolymer of polyvinylpyrrolidone and vinyl acetate is present in an amount of from about 2 weight percent to about 10 weight percent, wherein the total components equal 100 weight percent.

10. The drug delivery system of any of paragraphs 1 through 4, wherein the silicon dioxide is present in an amount of from about 2% to about 15% weight percent, wherein the total components equal 100 weight percent.

11. The drug delivery system of any of paragraphs 1 through 4, wherein the sodium stearyl fumarate or magnesium stearate is present in an amount of from about 0.25 weight percent to about 7.5 weight percent, wherein the total components equal 100 weight percent.

12. The drug delivery system of any of paragraphs 1 through 11, wherein the polyvinyl pyrrolidone is present in an amount of from about 5 weight percent to about 12 weight percent, the copolymer of polyvinylpyrrolidone and vinyl acetate is present in an amount of from about 0.5 weight percent to about 5 weight percent and the silicon dioxide is present in an amount of from about 5 weight percent to about 12 weight percent, wherein the total components equal 100 weight percent.

13. The drug delivery system of any of paragraphs 1 through 12, further comprising a polyoxyethylene-polyoxypropylene copolymer.

14. The drug delivery system of paragraph 13, wherein the polyoxyethylene-polyoxypropylene copolymer is present in an amount from about 1% to about 10% weight percent, wherein the total components equal 100 weight percent.

15. The drug delivery system of any of paragraphs 1 through 14, further comprising a Biopharmaceutics Class II, a Class III or a Class IV active ingredient.

16. A drug delivery system comprising at least about 2 to about 15 percent of a glidant and a compound of Formula I:

or metabolites or pharmaceutically acceptable salts thereof.

17. The drug delivery system of paragraph 16, wherein the glidant is silicon dioxide.

18. The drug delivery system of paragraph 17 further comprising:
sodium lauryl sulfate
polyethylene glycol;
lactose;
cellulose;
crospovidone;
copovidone;
a polyoxyethylene-polyoxypropylene copolymer;
and sodium stearyl fumarate or magnesium stearate.

19. The drug delivery system of paragraph 16 wherein the compound of Formula I is present in amount from 10 to 40 percent by weight.

20. The drug delivery system of paragraph 18, wherein the sodium lauryl sulfate or polyethylene glycol is present in an amount from about 0.5 to about 3 percent or from about 2 to about 10 percent by weight, respectively.

21. The drug delivery system of paragraph 18, wherein the polyethylene glycol is present in an amount from 2 to about 10 percent by weight.

22. The drug delivery system of paragraph 18, wherein the lactose is present in an amount from about 5 to about 20 percent by weight.

23. The drug delivery system of paragraph 18, wherein the cellulose is present in an amount from about 15 to about 60 percent by weight.

24. The drug delivery system of paragraph 18, wherein the crospovidone is present in an amount from about 5 to about 20 percent by weight.

25. The drug delivery system of paragraph 18, wherein the copovidone is present in an amount from about 0.2 to about 2 percent by weight.

26. The drug delivery system of paragraph 18, wherein the polyoxyethylene-polyoxypropylene copolymer is present in an amount from about 2 to about 5 percent by weight.

27. The drug delivery system of paragraph 18, wherein the sodium stearyl fumarate or magnesium stearate is present in an amount from about 0.5 to about 5 percent by weight.

28. The drug delivery system of paragraph 15, wherein the Biopharmaceutics Class II, a Class III or a Class IV active ingredient is 2-amino-N-(4-(5-(phenanthren-2-yl)-3-(trifluoromethyl)-1H-pyrazol-1-yl)phenyl)acetamide.

29. A composition comprising the compound having Formula I (I)

at least about 2 to about 15% silicon dioxide, and a pharmaceutically acceptable carrier.

30. The composition of paragraph 29, wherein the bioavailability of the compound of Formula I is greater than 20.

31. The composition of paragraph 30, wherein the bioavailability of the compound of Formula I is at least about 50.

32. A method of making a drug delivery system, comprising the steps of:
mixing a compound having Formula I sodium lauryl sulphate or polyethylene glycol, and a polyoxyethylene-polyoxypropylene copolymer to form mixture I;
adding crospovidone or copovidone, lactose, cellulose, and a glidant to mixture I to form mixture II;
adding sodium stearyl fumarate to mixture II to form mixture III; and
compressing mixture III to form a tablet.

33. The method of paragraph 32, wherein the glidant is silicone dioxide.

34. The method of paragraph 33, wherein silicone dioxide is present in an amount from about 2 to about 15 percent.

35. The method of paragraph 34, wherein the amount of silicone dioxide is about 7 to about 10 percent.

36. The method of paragraph 32 wherein the compound of Formula I is present in an amount from about 10 to 40 percent by weight, sodium lauryl sulphate or polyethylene glycol is present in an amount from about 0.5 to about 3 percent by weight, a polyoxyethylene-polyoxypropylene copolymer is present in an amount from about 2 to about 5 percent by weight, crospovidone is present in an amount from about 5 to about 20 percent, copovidone is present in an amount from about 0.2 to about 2 percent by weight, lactose is present in an amount from about 5 to about 20 percent by weight, cellulose is present in an amount from about 15 to about 60 percent by weight, and silicone dioxide is present in an amount from about 2 to about 15 percent.

EXAMPLES

The following examples are illustrative, but not limiting, of the formulations and methods of the present invention. Other suitable modifications and adaptations of the variety of conditions and parameters normally encountered in clinical therapy and which would be understood by those skilled in the art are within the spirit and scope of the invention.

Example 1

An exemplary solid pharmaceutical dosage form comprising the compound of Formula I below, also known as 2-amino-N-(4-(5-(phenanthren-2-yl)-3-(trifluoromethyl)-1H-pyrazol-1-yl)phenyl)acetamide and referred to herein as AR-12 was prepared using the components of Table 1 in the quantities listed (Formulation A). In one aspect, AR-12 has a molecular weight (free base) of 460.45, and a formula weight (HCl salt) of 496.91. In another aspect, the solubility of AR-12 in (1) USP chloride buffer at pH 1.2 is 65.34 ug/ml, (2) USP bipthalate buffer at pH 3.5 is 0.18 ug/ml, (3) UPS biphthalate buffer at pH 5 is 0.07 ug/ml, and (4) USP phosphate buffer at pH 7.4 is 0.06 ug/ml. In another aspect, the free base and HCl salt forms of AR-12 have the following structures:

(I)

Mol. Wt.: 460.45
AR-12

-continued

Mol. Wt.: 496.91
AR-12 HCl Salt

Table 1 lists two exemplary 100 mg tablet formulations (Formulation A and Formulation B) prepared according to the following exemplary process: (1) Prior to dispensing, screen all the excipients through a #20 mesh screen and Sodium Stearyl Fumarate through a #40 mesh hand screen. (2) Mix AR-12, Sodium Lauryl Sulphate or PEG 3350 and Lutrol Microprilled 127 in a polybag. (3) Add Crospovidone or Copovidone (Kolva 64) Fine, Lactose Fast Flo and Avicel pH 102, Colloidal silicon dioxide and mix manually. (4) Transfer Sodium Stearyl Fumarate into the polybag of step 3 and mix. (5) Compress the final blend on single station manual tablet press equipped with 12.0 mm or suitable round concave tooling.

TABLE 1

| ITEM NO. | INGREDIENT | QUANTITY (Formulation A) Wt. (%) | Qty/Tab mg | QUANTITY (Formulation B) Wt. (%) | Qty/Tab mg (Formulation B) |
|---|---|---|---|---|---|
| 1 | AR-12 HCl | 32.1 | 224.7* | 32.1 | 224.7* |
| 2 | SODIUM LAURYL SULFATE | 2.00 | 14.0 | | |
| 3 | Avicel pH-102 | 31.4 | 219.8 | 29.4 | 205.8 |
| 4 | LACTOSE FAST FLO | 10.0 | 70.0 | 10.0 | 70.0 |
| 5 | CROS-POVIDONE | 10.0 | 70.0 | 10.0 | 70.0 |
| 6 | COPOVIDONE (Kolva 64) Fine | 1.00 | 7.0 | — | — |
| 7 | COL. SILIC. DIOX. | 8.00 | 56.0 | 8.0 | 56.0 |
| 8 | Sodium stearyl fumarate | 1.5 | 10.5 | 1.5 | 10.5 |
| 9 | Polyethylene Glycol 3350 | — | — | 5.0 | 35.0 |
| 10 | Lutrol Microprilled 127 | 4.0 | 28.0 | 4.0 | 28.0 |
| TOTAL | | 100 | 700 | 100 | 700 |

*216 mg of AR-12 HCl = 200 mg of AR-12 base and quantity is compensated for 5% moisture present in AR-12 HCl.

In another exemplary process for making 100 mg tablets using Formulation C (shown below in Table 2), AR-12 or another active ingredient, sodium lauryl fumarate, and microcrystalline cellulose, were dry blended in a Bin Blender and Quadro Comil 196 (040G Screen). The resulting product ("Dry Blend I"), was then dry blended in a diffusion Blender with lactose, colloidal silicon dioxide, crospovidone, copovidone, and sodium stearyl fumarate to form "Dry Blend II."

Figure 1:
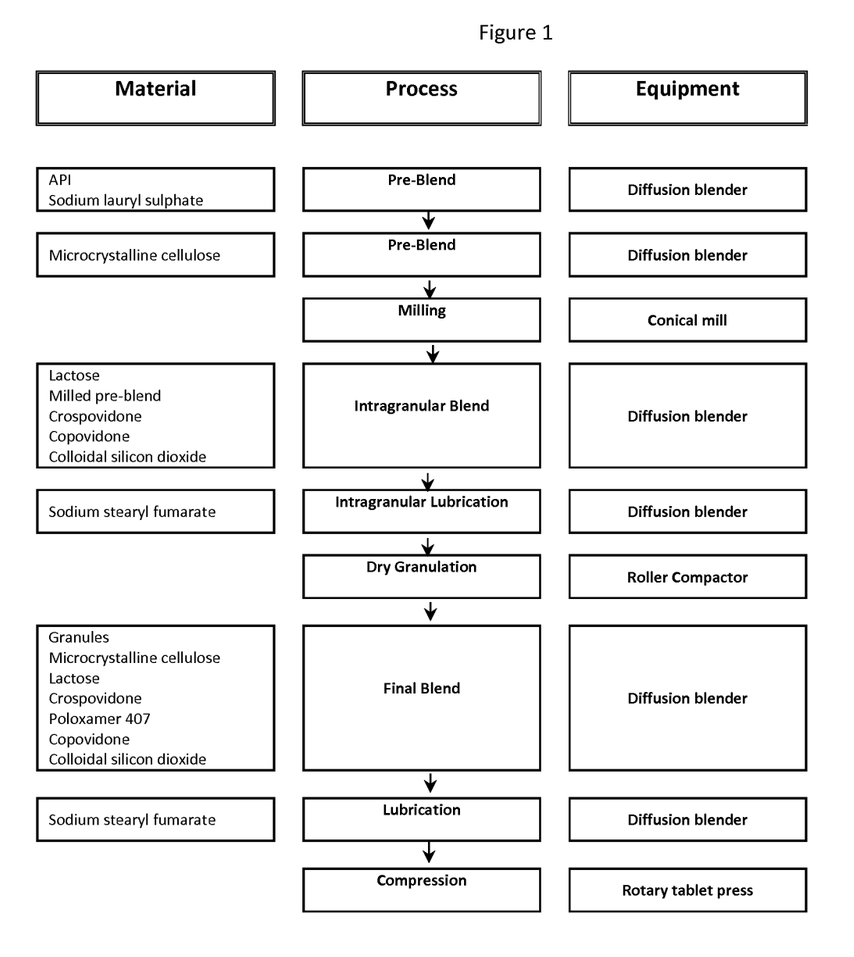
FIG. 1 provides an exemplary workflow diagram of one aspect described herein.
Figure 2:
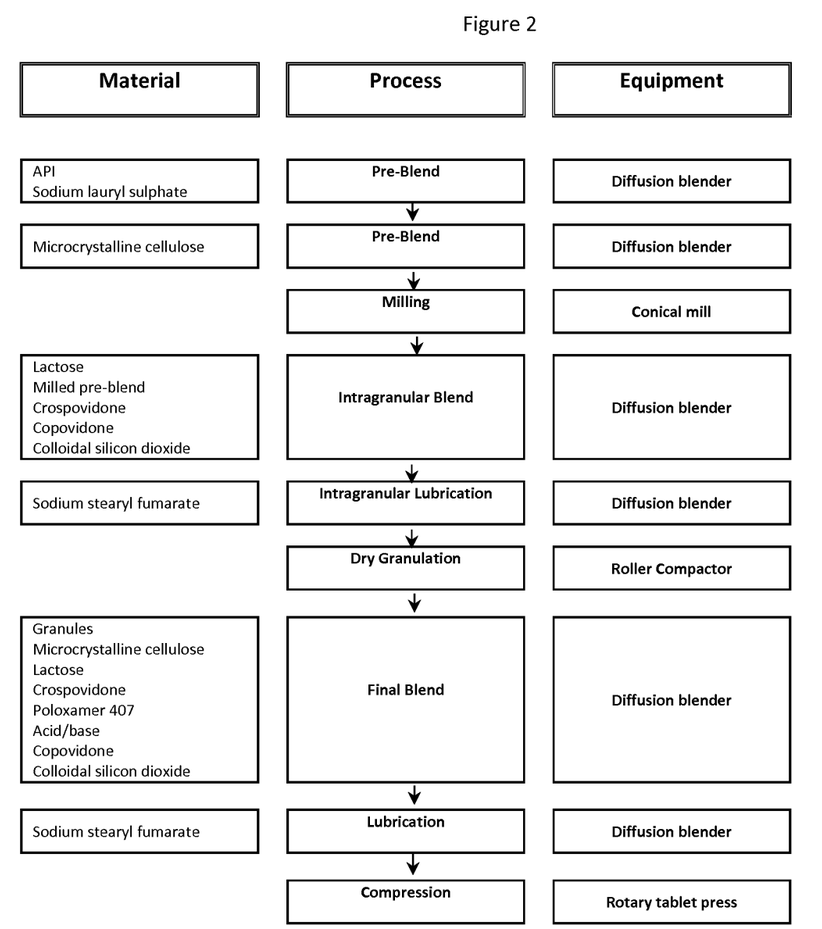
FIG. 2 provides a workflow diagram of another aspect described herein.
Figure 3:
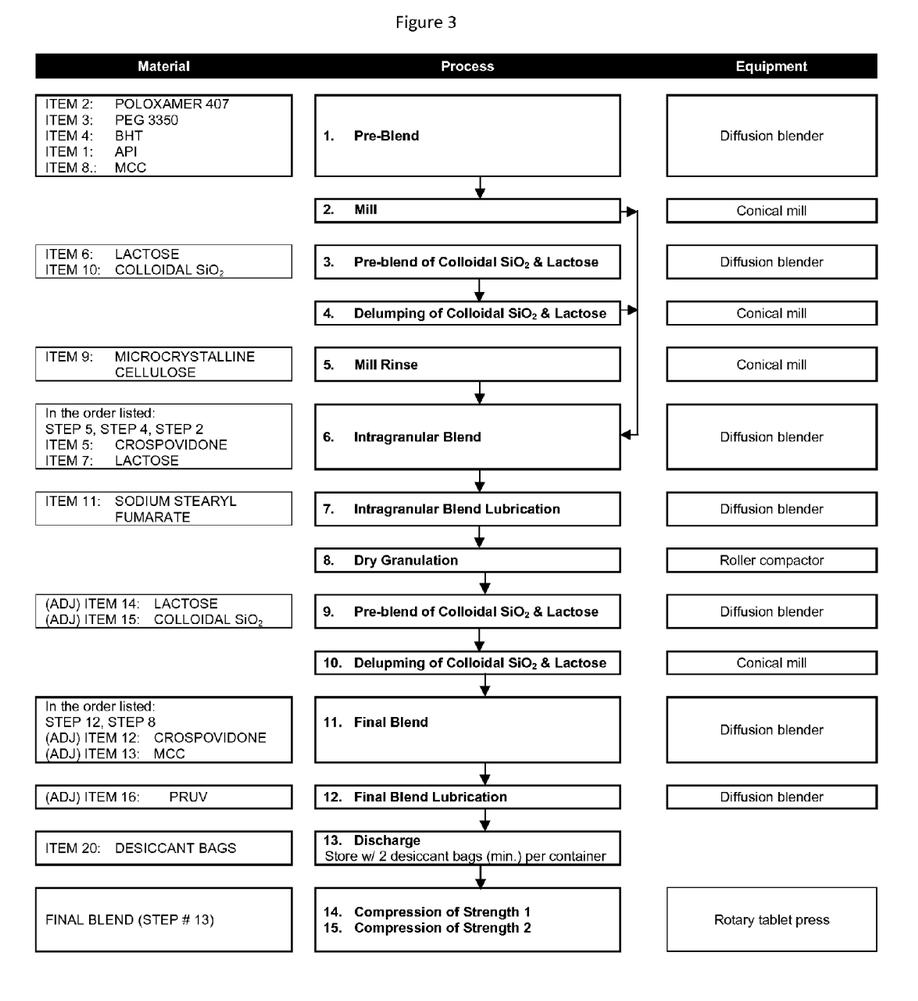
FIG. 3 provides a workflow diagram of still another aspect described herein.

Dry Blend II was then roller compacted to form Granules with the composition listed under "INTRAGRANULAR BLEND" in Table 2. The Granules were then dry blended in a diffusion Blender with microcrystalline cellulose, lactose, crospovidone, lutrol microprilled 127, copovidone, and colloidal silicon dioxide, in quantities listed under "EXTRAGRANULAR BLEND" in Table 2, to form a "Final Blend." The Final Blend was then lubricated with sodium stearyl sulfate, in the quantity listed under "EXTRAGRANULAR BLEND" in Table 2, using a diffusion mixture, such as a Bin Blender or V-Blender to form a "Lubricated Final Blend." The lubricated final blend was next compressed to form bulk tablets using a tablet press having 0.8600"×0.3440" bisected, modified capsule tooling size D. FIGS. 1 through 4 provide examples of various aspects of the process and compositions of the carrier systems used herein.

TABLE 2

| ITEM NO. | mg/Tablet | CODE | INGREDIENT | QUANTITY | UNITS |
|---|---|---|---|---|---|
| INTRAGRANULAR BLEND | | | | | |
| 1 | 172.0 | | Active Pharmaceutical Ingredient | 12.9 | kg |
| 2 | 22.0 | | SODIUM LAURYL SULFATE | 1.650 | kg |
| 3 | 202.1 | | MICRO-CRYSTALLINE CELLULOSE | 15.158 | kg |
| 4 | 130.6 | | LACTOSE FAST FLO | 9.795 | kg |
| 5 | 137.5 | | CROS-POVIDONE | 10.313 | kg |
| 6 | 7.3 | | COPOVIDONE | 547.5 | g |
| 7 | 27.5 | | COL. SILIC. DIOX. | 2.063 | kg |
| 8 | 9.9 | | Sodium stearyl fumarate | 742.5 | g |
| EXTRAGRANULAR BLEND | | | | | |
| 9 | 103.3 | | Microcrystalline CELLULOSE | 7.748 | kg |
| 10 | 65.2 | | LACTOSE | 4.890 | kg |
| 11 | 137.5 | | CROS-POVIDONE | 10.313 | kg |
| 12 | 44.0 | | LUTROL MICROPRILLED 127 | 3.300 | kg |
| 13 | 3.7 | | COPOVIDONE | 277.5 | g |
| 14 | 27.5 | | Colloidal silicon dioxide | 2.063 | kg |
| 15 | 9.9 | | Sodium stearyl fumarate | 742.5 | g |
| TOTAL | 1100.0 | | | 82.5 | kg |

Example 2

An animal study was conducted to obtain pharmacokinetic (PK) parameter data for eight dosage forms of AR-12 in beagle dogs. The following dosage forms were provided in an eight period, eight formulation, and non-GLP study to eight fasting beagle dogs: I (Injection, II (Solutol capsules), III (Labrosol capsules), IV (Tablets), V (Capsules from Mississippi), VI (Poloxamer 188 capsules), VII (Solutol+TPGS capsules), VII (Poloxamer+Acdisol capsules). As shown in Table 3 below, C. (maximum or peak blood concentration), $t_{max}$ (time to maximum or peak blood concentration), $AUC_{0-t}$ (area under the curve), $AUC_{0-\infty}$, $T_{1/2}$ (half life in blood), and F (bioavailability represented by the ratio of the AUC after oral administration compared to the AUC from normalized intravenous administration) were measured for each dosage form. While forms II, III, and VIII showed an F value above 20, the stability of these formulations was not optimal. Form IV (Tablets) represents the clinical formulation for AR-12 with a bioavailability (F) value of 20.7.

TABLE 3

| Phase | $C_{max}$ (ng/ml) | $t_{max}$ (h) | $AUC_{0-t}$ (ng/ml * h) | $AUC_{0-\infty}$ | $T_{1/2\,h}$ | F |
|---|---|---|---|---|---|---|
| I (Injection) | 2644 | 0.091 | 7727 | 8736 | 15.4 | 100.0 |
| II (Solutol capsules) | 679 | 4 | 15387 | 17545 | 15.33 | 53.3 |
| III (Labrosol capsules) | 377 | 8.75 | 10255 | 19635 | 28.0 | 34.3 |
| IV (Tablets) | 235 | 9 | 6706 | 9936 | 26.9 | 20.7 |
| V (Hot melt extrudate) | 179 | 9 | 4513 | 6999 | 19.6 | 14.5 |
| VI (Poloxamer 188 capsules) | 299 | 6 | 7053 | 8292 | 15.8 | 22.8 |
| VII (Solutol + TPGS capsules) | 377 | 3.25 | 3517 | 4434 | 20.6 | 11.8 |
| VIII (Poloxamer + Acdisol capsules) | 447 | 4.25 | 10927 | 12497 | 15.6 | 36.0 |

A second animal study was conducted in eight beagle dogs orally administered six AR-12 formulations: Formulation A (Intravenous), Formulation B (200 mg Liquid Filled Capsule), Formulation C (200 mg Liquid Filled Capsule), Formulation D (200 mg Liquid Filled Capsule), Formulation E (200 mg tablet formulation of Table 1), Formulation F (200 mg table formulation of Table 1).

The liquid filled capsule formulations did not exhibit optimal stability (See, e.g., Table 5 below) although the bioavailability (F) for the liquid filled capsules were all above 50. Formulations E and F (AR-12 tablet formulations corresponding to Table 1 above), however, had excellent stability and bioavailability (F) values (50.1 and 44.8 respectively, highlighted in Table 4 below) 150% greater than the clinical AR-12 tablet formulation shown in Table 3 (F value of 20.7).

TABLE 4

| Bengle Dog's No | $AUC_{(0-t)}$ (ng/h/mL) | | | | | | F (%) | | | | |
|---|---|---|---|---|---|---|---|---|---|---|---|
| | A (after normalized) | B | C | D | E | F | B | C | D | E | F |
| 1 | 46065 | 18852 | 15150 | 16147 | 12880 | 12822 | 70.8 | 56.9 | 60.7 | 48.4 | 48.2 |
| 2 | 34477 | 18281 | 11774 | 14672 | 18571 | 23293 | 58.3 | 37.5 | 46.8 | 59.2 | 74.2 |
| 3 | 30330 | 21031 | 19820 | 25419 | 11551 | 11799 | 65.4 | 61.6 | 79.0 | 35.9 | 36.7 |
| 4 | 22187 | 20339 | 26493 | 23099 | 9852 | 21680 | 62.4 | 81.3 | 70.9 | 30.2 | 66.6 |
| 5 | 19932 | 10196 | 14002 | 11135 | — | — | 46.1 | 63.4 | 50.4 | — | — |
| 6 | 39184 | 18818 | 25031 | 24259 | 18223 | 8356 | 48.8 | 64.9 | 62.9 | 47.2 | 21.7 |
| 7 | 22337 | 13682 | 16224 | 11484 | 20173 | 7017 | 40.0 | 47.5 | 33.6 | 59.0 | 26.5 |
| 8 | 32744 | 12349 | 17804 | 16045 | 17019 | 11066 | 51.4 | 74.1 | 66.8 | 70.8 | 46.1 |
| Mean | 30907 | 16693 | 18287 | 17782 | 15467 | 13719 | 55.4 | 60.9 | 58.9 | 50.1 | 44.8 |
| SD | 9139 | 4035 | 5214 | 5704 | 3985 | 6328 | 10.5 | 13.9 | 14.6 | 14.1 | 20.6 |

TABLE 5

| | Total Impurities | |
|---|---|---|
| Formulation | T-0 | 1 month 40 C./75% RH |
| B | 0.22 | 0.31 |
| C | 0.29 | 0.52 |
| D | 0.27 | 0.55 |

All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing has been described in some detail by way of illustration and example for purposes of clarity of understanding, it will be understood that certain changes and modifications may be practiced within the scope of the appended claims.

What is claimed is:

1. A drug delivery system comprising:
   sodium lauryl sulfate or a polyethylene glycol;
   cellulose;
   lactose;
   polyvinylpyrrolidone;
   a copolymer of polyvinylpyrrolidone and vinyl acetate;
   a silicon dioxide present in an amount of from about 4 weight percent to about 15 weight percent;
   and sodium stearyl fumarate or magnesium stearate, wherein the total components equal 100 weight percent, wherein the silicon dioxide increases the bioavailability of biopharmaceutic class II, III, or IV active agents.

2. The drug delivery system of claim 1, wherein the silicon dioxide is colloidal silicon dioxide.

3. The drug delivery system of claim 1, wherein the cellulose is microcrystalline cellulose.

4. The drug delivery system of claim 2, wherein the sodium lauryl sulfate or polyethylene glycol is present in an amount of from about 0.5 weight percent to about 6 weight percent.

5. The drug delivery system of claim 3, wherein the sodium lauryl sulfate or polyethylene glycol is present in an amount of from about 0.5 weight percent to about 6 weight percent.

6. The drug delivery system of claim 2, wherein the cellulose is present in an amount of from about 20 weight percent to about 70 weight percent.

7. The drug delivery system of claim 3, wherein the cellulose is present in an amount of from about 20 weight percent to about 70 weight percent.

8. The drug delivery system of claim 2, wherein the lactose is present in an amount of from about 10 weight percent to about 40 weight percent.

9. The drug delivery system of claim 3, wherein the lactose is present in an amount of from about 10 weight percent to about 40 weight percent.

10. The drug delivery system of claim 2, wherein the polyvinyl pyrrolidone is present in an amount of from about 5 weight percent to about 25 weight percent.

11. The drug delivery system of claim 3, wherein the polyvinyl pyrrolidone is present in an amount of from about 5 weight percent to about 25 weight percent.

12. The drug delivery system of claim 2, wherein the copolymer of polyvinylpyrrolidone and vinyl acetate is present in an amount of from about 2 weight percent to about 10 weight percent.

13. The drug delivery system of claim 3, wherein the copolymer of polyvinylpyrrolidone and vinyl acetate is present in an amount of from about 2 weight percent to about 10 weight percent.

14. The drug delivery system of claim 2, wherein the sodium stearyl fumarate or magnesium stearate is present in an amount of from about 0.25 weight percent to about 7.5 weight percent.

15. The drug delivery system of claim 3, wherein the sodium stearyl fumarate or magnesium stearate is present in an amount of from about 0.25 weight percent to about 7.5 weight percent.

16. The drug delivery system of claim 2, wherein the polyvinyl pyrrolidone is present in an amount of from about 5 weight percent to about 12 weight percent, the copolymer of polyvinylpyrrolidone and vinyl acetate is present in an amount of from about 0.5 weight percent to about 5 weight percent.

17. The drug delivery system of claim 3, wherein the polyvinyl pyrrolidone is present in an amount of from about 5 weight percent to about 12 weight percent, the copolymer of polyvinylpyrrolidone and vinyl acetate is present in an amount of from about 0.5 weight percent to about 5 weight percent.

18. The drug delivery system of claim 2, further comprising a polyoxyethylene-polyoxypropylene copolymer.

19. The drug delivery system of claim 3, further comprising a polyoxyethylene-polyoxypropylene copolymer.

20. A drug delivery system comprising:
sodium lauryl sulfate or a polyethylene glycol;
cellulose;
lactose;
polyvinylpyrrolidone;
a copolymer of polyvinylpyrrolidone and vinyl acetate;
a silicon dioxide;
and sodium stearyl fumarate or magnesium stearate, wherein the polyvinyl pyrrolidone is present in an amount of from about 5 weight percent to about 12 weight percent, the copolymer of polyvinylpyrrolidone and vinyl acetate is present in an amount of from about 0.5 weight percent to about 5 weight percent and the silicon dioxide is present in an amount of from about 5 weight percent to about 12 weight percent, wherein the total components equal 100 weight percent, and wherein the silicon dioxide increases the bioavailability of biopharmaceutic class II, III, or IV active agents.

* * * * *